United States Patent [19] [11] 4,137,415
Panzer et al. [45] Jan. 30, 1979

[54] PROCESS FOR PREPARATION OF 2-VINYLIMIDAZOLINES

[75] Inventors: Hans P. Panzer, Stamford; Kenny U. Acholonu, Bridgeport, both of Conn.

[73] Assignee: American Cyanamid Company, Stamford, Conn.

[21] Appl. No.: 867,255

[22] Filed: Jan. 5, 1978

[51] Int. Cl.² .......................................... C07D 233/06
[52] U.S. Cl. .................................................. 548/347
[58] Field of Search ......................................... 548/347

[56] References Cited

U.S. PATENT DOCUMENTS 3,360,506  12/1967  De Benneville et al. ....... 548/347 X
4,074,055  2/1978   Panzer et al. ...................... 548/347

*Primary Examiner*—Richard Raymond
*Attorney, Agent, or Firm*—William J. van Loo

[57] ABSTRACT

2-vinyl-2-imidazolines are prepared by cleaving 2-acylamidoethyl-2-imidazolines at suitable temperature, distilling the cleavage products, and recovering the desired product from the distillate.

5 Claims, No Drawings

PROCESS FOR PREPARATION OF 2-VINYLIMIDAZOLINES

CROSS-REFERENCE TO RELATED APPLICATIONS

This application is related to applications Ser. Nos. 867,252 and 867,251, filed on even date herewith. The instant application relates to the preparation of 2-vinyl-2-imidazolines. Ser. No. 867,252 relates to 2-acylamidoethyl-2-imidazoles which are cleaved in the present application and Ser. No. 867,351 relates to a process for preparing 2-acylamidoethyl-2-imidazolines.

This invention relates to a process for preparing 2-vinyl-2-imidazolines. More particularly, this invention relates to such a process wherein a 2-acylamidoethyl-2-imidazoline is cleaved to provide the desired 2-vinyl-2-imidazoline.

The need for high efficiency products for use in the treatment of aqueous suspensions of solids has continued to grow in recent years because of the increasing awareness of the environment pollution caused by such substances and other considerations. Accordingly, there have been increased efforts expended in attempts to provide such products which can be used to facilitate the dewatering of aqueous suspensions of organic, or mixtures of organic and inorganic materials, such as distillery wastes, fermentation wastes, wastes from paper manufacturing plants, dye plant wastes, and sewage suspension such as digested sludges, activated sludges, or raw and primary sludges from sewage treatment plants as well as a host of other suspension types.

The more recent and more successful materials used in the treatment of such suspensions have been amidine or imidazoline polymers, see U.S. Pat. Nos. 3,406,139; 3,450,646; 3,576,740 and 3,666,705. Such polymers are very effective materials for use in the treatment of industrial wastes. The polymers are produced, however, by the treatment of corresponding nitrile polymers and are therefore governed by the structure of the nitrile polymers. Furthermore, conversion of the nitrile polymers to the imidazoline or amidine form does not reach 100% and therefore a portion of the resultant polymer is in improper form to function in water treating capacity.

Prior attempts to obviate these difficulties have included rearrangement of the groups present in the nitrile charge polymer and the attempted production of unsaturated imidazolines and amides which may be homopolymerized or copolymerized into more active imidazoline and amidine polymers. However, attempts to produce intermediates, from which the unsaturated imidazolines and amidines may be prepared have proven unsuccessful. Furthermore, attempts to follow the teachings of U.S. Pat. No. 3,210,371 resulted only in the production of undesired polymeric material and the teachings of Oxley et al., J. Chem. Soc. 1947, page 497–505, also resulted in the recovery of undesired polymeric products. Recent developments are typified by U.S. Pat. Nos. 4,006,247 and 4,007,200. In U.S. Pat. No. 4,007,200, there are disclosed intermediates which require numerous preparative steps which are difficult to perform, thus complicating processing and reducing yields of the intermediate. In U.S. Pat. No. 4,006,247, it is disclosed that the intermediates of U.S. Pat. No. 4,007,200 can be cracked to provide unsaturated imidazolines and amidines. However, the intermediate is unstable in cracking, thus reducing yields of unsaturated compounds. The cracking process is difficult to perform and undesirable.

There continues to exist the need for a process for unsaturated imidazolines which is free of deficiencies of former processes and provides such compounds by simple processing. Such a provision would fulfill a long-felt need and constitute a notable advance in the art.

In accordance with the present invention, there is provided a process for preparing compounds of the structure:

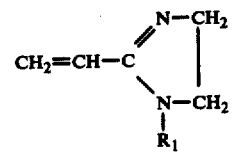

wherein $R_1$ is hydrogen or an alkyl group of about 1 to 5 carbon atoms, said process comprising heating to cracking temperature a compound of the structure:

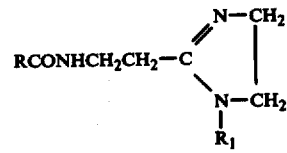

wherein R is an alkyl group of about 1 to 5 carbon atoms and $R_1$ is hydrogen or an alkyl group of about 1 to 5 carbon atoms, distilling the cleavage products, and recovering the desired compound from the distillate.

The process of the present invention provides 2-vinyl-2-imidazolines in monomer form which can be readily processed to the desired polymers for the various uses previously mentioned. The present process employs stable intermediates which enable the desired vinylimidazoline monomers to be distilled from the reaction vessel under vacuum.

In carrying out the process of the present invention, the starting intermediate is a 2-acylamidoethyl-2-imidazoline of the structure:

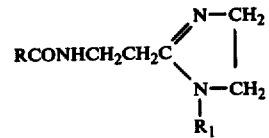

wherein R is an alkyl group of about 1 to 5 carbon atoms and $R_1$ is hydrogen or an alkyl group of about 1 to 5 carbon atoms. The 2-acylamidoethyl-2-imidazolines are readily prepared by reacting a 2-cyanoethylacylamide with a suitable ethylenediamine in equal molar proportions under conditions such that one molar equivalent of $NH_3$ is evolved and ring closure results. The 2-cyanoethylacylamides are well-known in the art and are obtained by reacting an acylamide with acrylonitrile in the presence of a strong alkali. The reaction is described in the Chemistry of Acrylonitrile, IV Cyanoethylation of Active Hydrogen Groups, Bruson and Riener, J. Am. Chem. Soc., 65, page 23 (1943). This reaction is given by the equation $RCONH_2 + CH_2 = CHCN \xrightarrow{alkali} RCONHCH_2CH_2CN$. For purposes of the present invention, R is an alkyl group of about 1 to 5 carbon atoms.

Using a selected 2-cyanoethylacylamide as described, the desired 2-acylamidoethyl-2-imidazoline is prepared by reaction with an ethylenediamine of the structure $R_1HNCH_2CH_2NH_2$ wherein $R_1$ is hydrogen or an alkyl group of about 1 to 5 carbon atoms, preferably in the presence of a suitable catalyst. A preferred catalyst is sulfur. The reaction is carried out at an elevated temperature to minimize reaction time but at a temperature safely below that at which decomposition occurs. Reaction is quite rapid, generally 90 minutes or less at 115° C. A solvent may be used if desired but reaction can be effected in the absence of solvent. The crude product obtained is readily purified by recrystallization, for example, and yields of pure product are 70% or higher. The reaction follows the equation

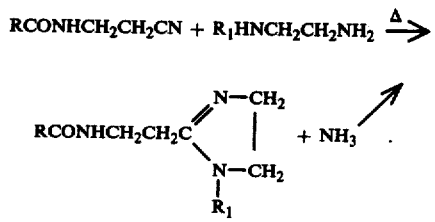

The reactants are generally employed in equal molar amounts. If a catalyst is employed it is used in effective amount. Preferably, sulfur is used at a concentration of about 0.5 to 1.0 weight percent based on the weight of reactants. As indicated, a solvent may be used if desired and, if used, should generally be in an amount providing suitable fluidity to the reaction mixture. A preferred solvent is toluene.

2-acylamidoethyl-2-imidazolines are readily cleaved according to the process of the present invention to 2-vinyl-2-imidazolines. In carrying out the process of the present invention, the 2-acylamidoethyl-2-imidazoline is one having the general structure:

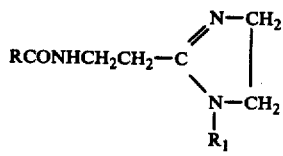

wherein R is an alkyl group of about 1 to 5 carbon atoms and $R_1$ is hydrogen or an alkyl group of about 1 to 5 carbon atoms.

The selected 2-acylamidoethyl-2-imidazoline is heated to cracking temperature, to provide a 2-vinyl-2-imidazoline and an acylamide according to the reaction

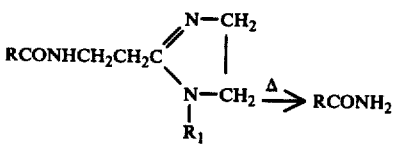

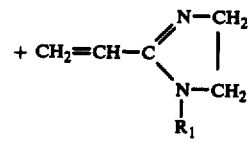

The cleavage products are distilled and since the 2-vinyl-2-imidazoline has a lower boiling temperature than the acylamide, it constitutes a major fraction of the distillate. The distillate is collected and the desired 2-vinyl-2-imidazoline is recovered from the distillate, generally as a suitable salt.

The invention is more fully illustrated by the examples which follow wherein all parts and percentages are by weight unless otherwise specified.

INTERMEDIATE PREPARATION

Preparation of 2-acetamidoethyl-2-imidazoline

To a 500 ml. round-bottomed flask equipped with a thermometer and reflux condenser were added 129.00 grams (1.15 mol) of 2-cyanoethylacetamide, 67.7 grams (1.13 mol) of ethylenediamine and 1.5 grams of sulfur. The reaction mixture was heated to 115° C. and held at that temperature for 90 minutes. Solidification of the reaction mixture occurred on cooling. The crude product weight 158 grams. It was recrystallized from 80 mol. of 2-propanol. 142 grams of pure product were obtained representing a yield of 81.2%. The product had a melting point of 137°–139° C.

EXAMPLE 1

Cleavage Of 2-Acetamidoethyl-2-Imidazoline

To a 250 ml. round-bottomed flask equipped with a distillation head, vacuum take-off adapter, and a receiver were added 22.2 grams (0.144 mol) of 2-acetamidoethyl-2-imidazoline prepared as described above, 70 grams of Carbowax 700, 4 grams of potassium hydroxide, 4.8 milligrams of Cupferon and 0.5 gram of phenothazine. The mixture was thoroughly mixed and heated to 200° C. at a pressure equivalent to 0.5 millimeters of mercury. At 80°–125° C. 2-vinyl-2-imidazoline codistilled with acetamide. 15.4 grams of product was isolated. NMR analysis of the bisulfate salt of 2-vinyl-2-imidazoline indicated a yield of 60%.

The recovered 2-vinyl-2-imidazoline was readily polymerized in aqueous solution to provide a high molecular weight polymer which showed excellent properties as a flocculant and dewatering agent.

EXAMPLE 2

In 4 milliliters of methanol was dissolved 1.5 grams of 2-acetamidoethyl-2-imidazoline and the resulting solution was passed through a 16 centimeter column of barium oxide impregnated on silica gel at 390° C. and a pressure equivalent to 23 millimeters of mercury. The 2-vinyl-2-imidazoline was collected as a light yellow solid in a 50 milliliter round-bottomed flask. The yield of 2-vinyl-2-imidazoline was 35% by nuclear magnetic resonance measured on the bisulfate salt.

EXAMPLE 3

The procedure of Example 1 was repeated in all essential details that hydrocarbon wax (M and M7334) was used instead of Celite. 2-vinyl-2-imidazoline was obtained in 50% yield (NMR).

EXAMPLE 4

The procedure of Example 1 was again followed except that Carbowax 600, 45 grams, was also employed. The yield of 2-vinyl-2-imidazoline was 68%.

EXAMPLE 5

The procedure of Example 1 was again repeated except that Carbowax 400, 70 grams, was also employed. The yield of 2-vinyl-2-imidazoline was 80%.

EXAMPLE 6

The procedure of Example 5 was followed reusing the Carbowax used in Example 5. The yield of 2-vinyl-2-imidazoline was 64%.

EXAMPLE 7

The procedure of Example 1 was again followed except Carbowax 400, 70 grams was used in place of Celite and sodium methoxide was used to replace the potassium hydroxide employed. The yield of 2-vinyl-2-imidazoline was 75%.

EXAMPLES 8 – 11

The following 2-acylamidoethyl-2-imidazolines were satisfactorily cracked followed the procedure of Example 1. The compounds and example number are listed below.

| Example No. | 2-acylamidoethyl-2-imidazoline | |
|---|---|---|
| | R-group | $R_1$-group |
| 8 | $C_2H_5$— | H— |
| 9 | $C_3H_7$— | $CH_3$— |
| 10 | $C_2H_5$— | $C_2H_5$— |
| 11 | $CH_3$— | $C_3H_7$— |

We claim:

1. A process for preparing compounds of the structure:

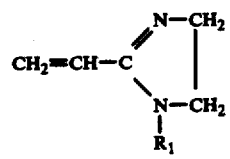

wherein $R_1$ is hydrogen or an alkyl of about 1 to 5 carbon atoms, said process comprising heating to cracking temperature a compound of the structure

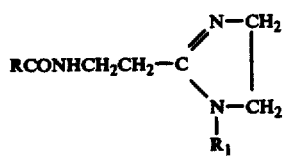

wherein R is an alkyl group of about 1 to 5 carbon atoms and $R_1$ is hydrogen or an alkyl group of about 1 to 5 carbon atoms distilling the cleavage products, and recovering the desired compound from the distillate.

2. The process of claim 1 wherein R is methyl and $R_1$ is hydrogen.

3. The process of claim 1 wherein R is ethyl and $R_1$ is hydrogen.

4. The process of claim 1 wherein R is propyl and $R_1$ is methyl.

5. The process of claim 1 wherein R is ethyl and $R_1$ is ethyl.